United States Patent
Chang

(10) Patent No.: US 7,371,733 B2
(45) Date of Patent: May 13, 2008

(54) ANTI BACTERIAL COMPOUNDS

(75) Inventor: Cheng-Wei Tom Chang, Logan, UT (US)

(73) Assignee: Utah State University, Logan, UT (US)

( * ) Notice: Subject to any disclaimer, the term of this patent is extended or adjusted under 35 U.S.C. 154(b) by 39 days.

(21) Appl. No.: 11/385,641

(22) Filed: Mar. 20, 2006

(65) Prior Publication Data

US 2006/0234961 A1    Oct. 19, 2006

(51) Int. Cl.
*A01N 43/04* (2006.01)
*A61K 31/70* (2006.01)
*C07H 15/24* (2006.01)
*C07H 15/22* (2006.01)

(52) U.S. Cl. ............... 514/38; 514/27; 514/35; 514/36; 536/4.1; 536/13.5; 536/16.6; 536/16.8; 536/18.1

(58) Field of Classification Search ............ None
See application file for complete search history.

(56) References Cited

OTHER PUBLICATIONS

Elchert et al., "Application of the Synthetic Aminosugars for Glycodiversification", J. Org. Chem., Jan. 28, 2004, vol. 69, pp. 1513-1523.*
Jinhua Wang, Jie Li, David Tuttle, Jon Y. Takemoto, Cheng-Wei Tom Chang; "The Synthesis of L-Aminosugar and the Studies of L-Pyranoses on the Ring III of Pyranmycins", Organic Letters, Oct. 15, 2002 (Web), pp. 3997-4000, vol. 4, No. 23, American Chemical Society, Washington, DC, USA.
Cheng-Wei Tom Chang, Yu Hui, Bryan Elchert, Jinhua Wang, Jie Li, and Ravi Rai; "Pyranmycins, a Novel Class of Aminoglycosides with improved Acid Stability: The SAR of D-Pyranoses on Ring III of Pyranmycin", Organic Letters, Nov. 21, 2002 (Web), pp. 4603-4606, vol. 4, No. 26, American Chemical Society, Washington, DC, USA.
Jie Li, Jinhua Wang, Yu Hui, Cheng-Wei Tom Chang; "Exploring the Optimal Site for Modifications of Pyranmycins with the Extended Arm Approach", Organic Letters, Jan. 24, 2003 (Web), pp. 431-434, vol. 5, No. 4, American Chemical Society, Washington, DC, USA.

* cited by examiner

*Primary Examiner*—Shaojia Anna Jiang
*Assistant Examiner*—Traviss C. McIntosh, III

(57) ABSTRACT

The invention relates to novel paranmycin compounds that have activity against gram positive and gram negative bacteria, preferably bacteria that are resistant to other antibiotics. Paranmycins are of the general formula

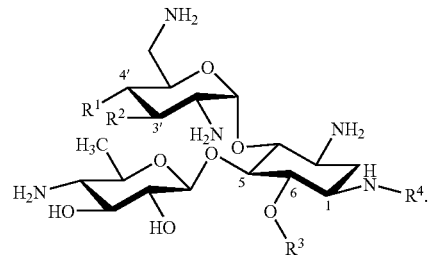

6 Claims, No Drawings

ANTI BACTERIAL COMPOUNDS

This research described in this patent application was partially funded by the National Institutes of Health (AI053138), and therefore the U.S. Government may have certain rights in the invention.

BACKGROUND

Aminoglycoside antibiotics have long been used as bactericidal drugs.[1] Unlike many antibiotics that are active only against gram positive bacteria, aminoglycosides have broad spectrum activity against both gram positive and negative bacteria. However, their clinical usage has often been limited only to serious infections due to the prevalence of aminoglycoside resistant bacteria[1c,2] and the high cytotoxicity of aminoglycosides.[3] In an effort to revive the effectiveness of aminoglycoside antibiotics against resistant bacteria, we have been working on modification and synthesis of novel aminoglycosides.

Over expression of aminoglycoside modifying enzymes from resistant bacteria is the most commonly encountered mode of resistance.[2] Various aminoglycoside modifying enzymes have been identified that catalyze a wide range of modifications including acetylation, phosphorylation, and adenylation.

Aminoglycosides with deoxygenation at 3'-OH have been demonstrated to be effective against APH(3') as reported by Umezawa[1b,6] and others.[7] The concept has led to the syntheses and discovery of tobramycin,[8] arbekacin,[9] and other similar aminoglycosides.[1b] Despite the fruitful results from these studies, there are several shortcomings. First, most of the research uses carbamate-type protecting groups for the protection of amino groups on the aminoglycoside, resulting in the formation of polycarbamate compounds with low solubility in organic media. The poor solubility of these compounds poses difficulties in their purification and characterization. Second, most of the syntheses begin with the kanamycin scaffold. There are very few examples of deoxygenation on neomycin class antibiotics.[7d] Third, the reported syntheses of both classes of antibiotics usually derive from kanamycin or neomycin, which limits the options for introducing novel structural motifs at other desirable places of aminoglycosides. Therefore, we have invented novel pyranmycin compounds with activity against resistant strains equipped with aminoglycoside modifying enzymes.

SUMMARY OF THE INVENTION

The invention relates to novel compounds that have activity against gram positive and gram negative bacteria, preferably bacteria that are resistant to other antibiotics. The compounds are derivatives of paranmycins.

Another aspect of the invention is the treatment of bacterial infections using the compounds of the invention.

DESCRIPTION OF THE CHARTS AND SCHEMES

The present invention contains no figures. However, Charts showing compounds and compound constituents and Schemes showing synthesis pathways are provided as summarized and described below.

Chart 1 shows a preferred group of pyranmycins with dideoxygenation.

Chart 2 shows a group of pyranmycins with N-1 modifications.

Chart 3 shows a group of pyranmycins with both dideoxygenation and N-1 modification.

Scheme 1 shows the synthesis of neamine acceptor.

Scheme 2 shows the synthesis of 3'-4'-Dideoxy Pyranmycin.

Scheme 3 shows synthesis of 3',4'-di-O-benzylneamine.

Scheme 4 shows One-pot synthesis of N-1 Modified Neamine.

Scheme 5 shows glycosylation of the hydroxyl group.

Scheme 6 shows current synthesis for pyranmycin with O-6 modification.

Scheme 7 shows synthesis of pyranmycin with n-1 and O-6 modifications.

DETAILED DESCRIPTION OF THE INVENTION

The present invention relates to antibacterial compound comprising a compound having Formula 1

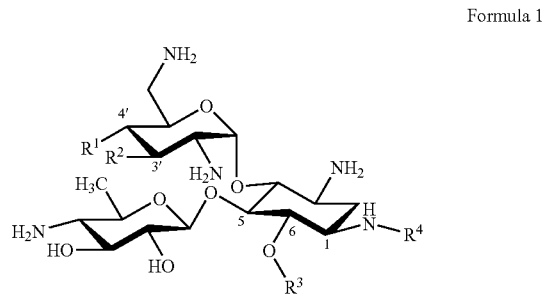

Formula 1 wherein
R1 and R2 are both either H or OH
R3 is selected from the group consisting of

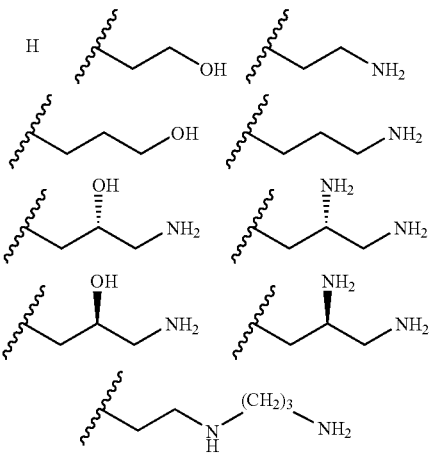

And R4 is either H or

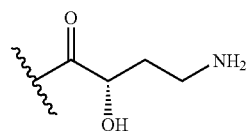

AHB: (S)-4-amino-2-hydroxybutyryl

More specifically, the compounds are of three different groups as shown in Charts 1, 2, and 3.
CHART 1
Pyranmycin with dideoxygenation
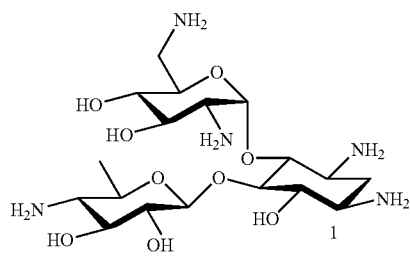
pyranmycin (TC005)
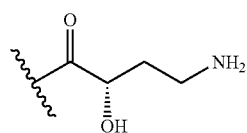
AHB: (S)-4-amino-2-hydroxybutyryl
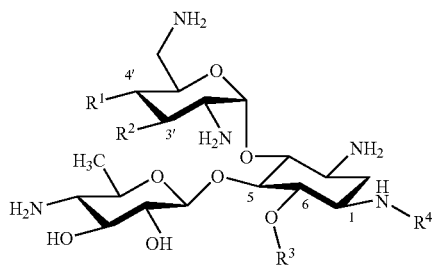
| $R^1$ | $R^2$ | $R^3$ | $R^4$ |
|---|---|---|---|
| H | H | H | H |
| H | H |  | H |
| H | H | 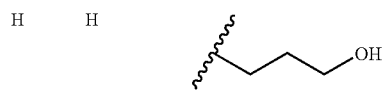 | H |
| H | H | 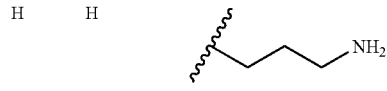 | H |
| H | H | (next page) | H |
CHART 1-continued
Pyranmycin with dideoxygenation
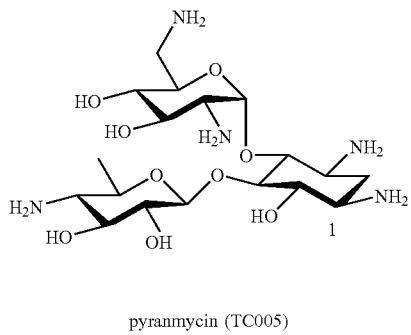
pyranmycin (TC005)
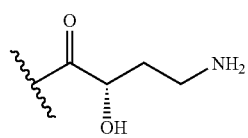
AHB: (S)-4-amino-2-hydroxybutyryl
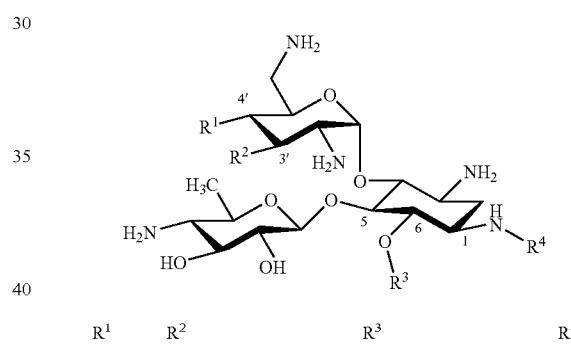
| $R^1$ | $R^2$ | $R^3$ | $R^4$ |
|---|---|---|---|
| H | H | 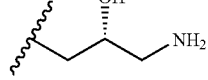 | H |
| H | H | 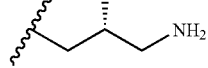 | H |
| H | H | 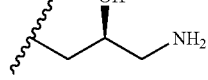 | H |
| H | H | 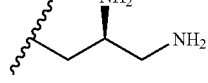 | H |
| H | H | 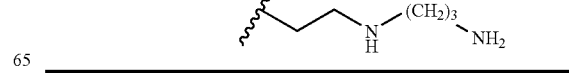 | H |

CHART 2
Pyranmycin with N-1 Modification
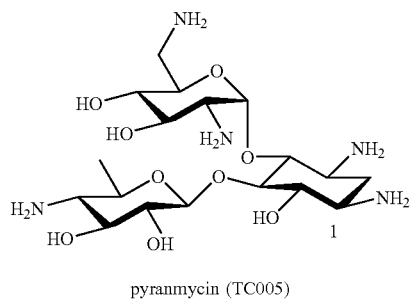
pyranmycin (TC005)
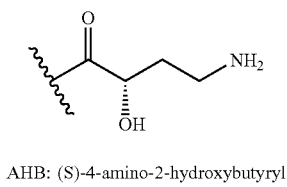
AHB: (S)-4-amino-2-hydroxybutyryl
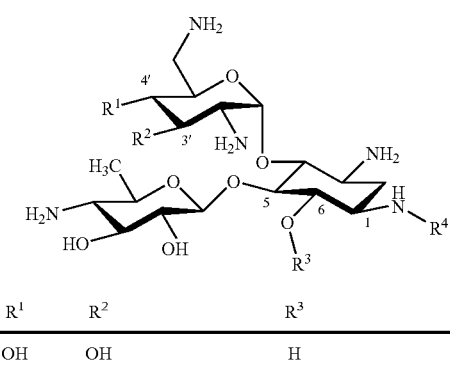
| R¹ | R² | R³ | R⁴ |
|---|---|---|---|
| OH | OH | H | AHB |
| OH | OH | 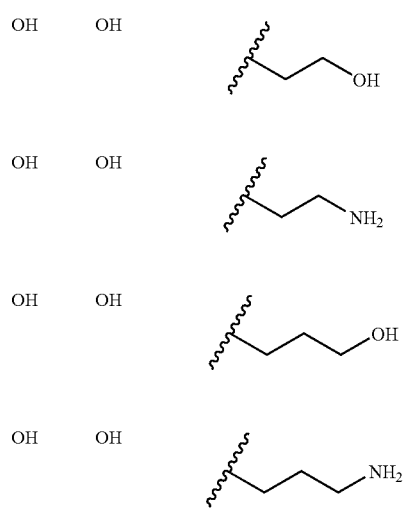 | AHB |
| OH | OH | | AHB |
| OH | OH | | AHB |
| OH | OH | | AHB |
| OH | OH | | AHB |
CHART 2-continued
Pyranmycin with N-1 Modification
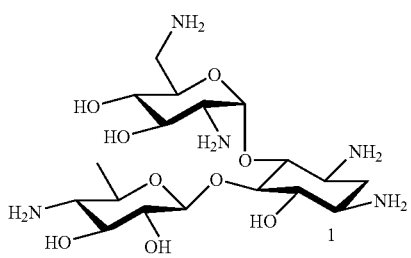
pyranmycin (TC005)
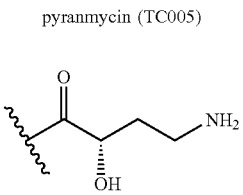
AHB: (S)-4-amino-2-hydroxybutyryl
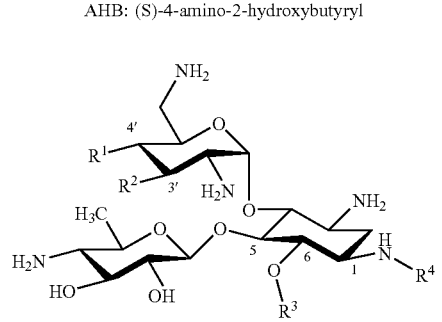
| R¹ | R² | R³ | R⁴ |
|---|---|---|---|
| OH | OH | 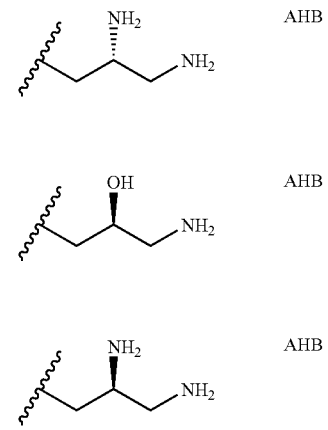 | AHB |
| OH | OH | | AHB |
| OH | OH | | AHB |
| OH | OH | | AHB |

CHART 3

Pyranmycin with combined deoxygenation and N-1 Modification

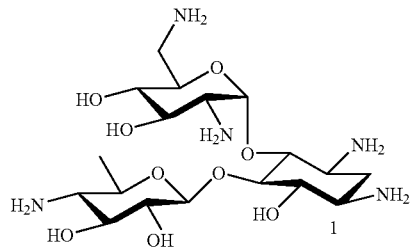

pyranmycin (TC005)

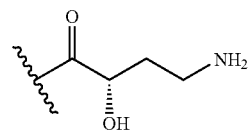

AHB: (S)-4-amino-2-hydroxybutyryl

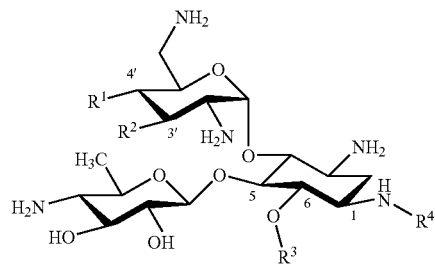

| R¹ | R² | R³ | R⁴ |
|---|---|---|---|
| H | H | H | AHB |
| H | H | ⁓⁓⁓CH₂CH₂OH | AHB |
| H | H | ⁓⁓⁓CH₂CH₂NH₂ | AHB |
| H | H | ⁓⁓⁓(CH₂)₃OH | AHB |
| H | H | ⁓⁓⁓(CH₂)₃NH₂ | AHB |
| H | H | ⁓⁓⁓CH₂CH(OH)CH₂NH₂ (S) | AHB |
| H | H | ⁓⁓⁓CH₂CH(NH₂)CH₂NH₂ (S) | AHB |

CHART 3-continued

Pyranmycin with combined deoxygenation and N-1 Modification

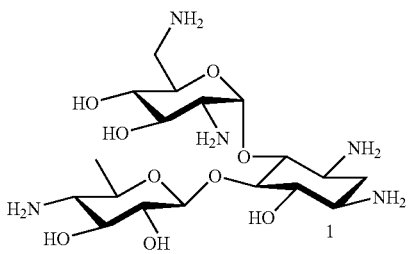

pyranmycin (TC005)

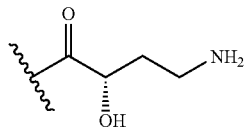

AHB: (S)-4-amino-2-hydroxybutyryl

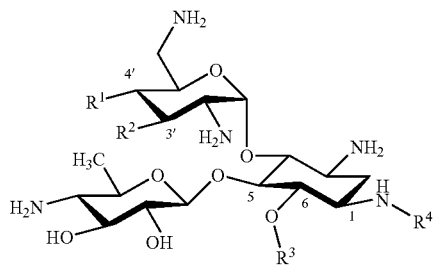

| R¹ | R² | R³ | R⁴ |
|---|---|---|---|
| H | H | ⁓⁓⁓CH₂CH(OH)CH₂NH₂ (R) | AHB |
| H | H | ⁓⁓⁓CH₂CH(NH₂)CH₂NH₂ (R) | AHB |
| H | H | ⁓⁓⁓CH₂CH₂NH(CH₂)₃NH₂ | AHB |

Preferably the compounds are selected from the group consisting of

[structure: RR501]

RR501

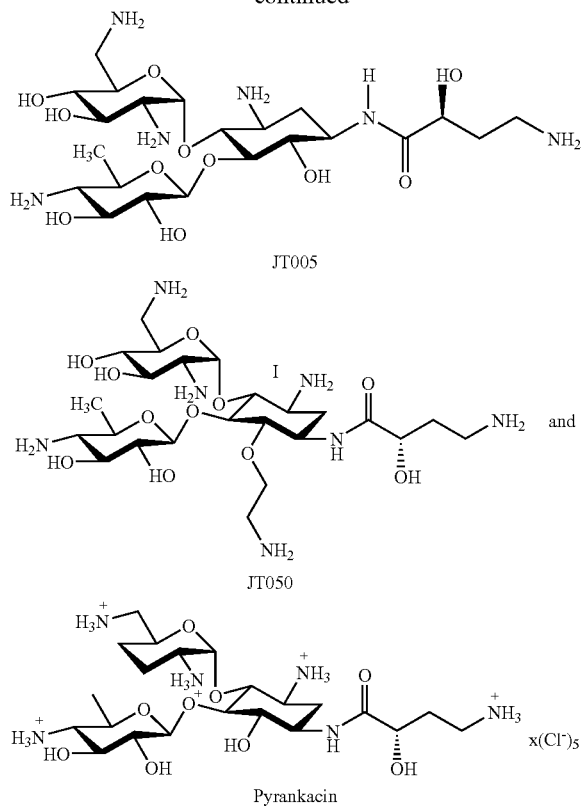

Generally, the compounds of the invention can be made using the starting materials of neomycin (Research Organics). The known reactions described in references 4 can be used to make the basic pyranmycin structure. Pyranmycin with hydroxyl groups at the 3' and 4' positions can by made using an elimination reaction. Substitution of the AHB on the amine position can be accomplished by using a selective Staudinger reaction followed by typical peptide coupling reaction. Substitution of any of the R3 substituents can result from selective alkylation reactions. Detailed synthesis of the compounds of the invention are provided in the examples, which are not meant to limit the scope of the present invention in any way.

Once made, the compounds of the present invention show anti bacterial activity in a standard dilution and diffusion assay. As such, the compounds of the present invention either alone or formulated into a pharmaceutically acceptable formulation, are useful as anti bacterial compounds to prevent, alleviate or eliminate the symptoms and/or organisms associated with a bacterial or viral infection. Preferably, the compounds are used for treating a bacterial infection.

Methods of Administration (Amts, Regimes)

The pharmaceutical compositions according to the invention are those for enteral (including oral or rectal) and parenteral (including intravenous, transdermal or intraarterial biodegradable stent) administration to a mammal, i.e. a warm-blooded animal or human. The daily dose of the active ingredients depends on the age and the individual condition and also on the manner of administration.

The pharmaceutical compositions contain, for example, from about 10% to about 80%, preferably from about 20% to about 60%, of the active ingredient. Pharmaceutical compositions according to the invention for enteral or parenteral administration are, for example, those in unit dose forms, such as sugar-coated tablets, tablets, capsules, gel caps, caplets, or suppositories, and furthermore ampoules. The compositions may also be in sublingual dosages, sustained release formulations and elixirs. These are prepared in a manner known per se, for example by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Suitable pharmaceutical carriers are, in particular, fillers, such as sugars, for example lactose, sucrose, mannitol or sorbitol, cellulose preparations and/or calcium phosphates, for example tricalcium phosphate or calcium hydrogen phosphate, furthermore binders, such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example, to identify or to indicate different doses of active ingredient, may be added to the tablets or sugar-coated tablet coatings.

Other orally utilizable pharmaceutical preparations are hard gelatin capsules, and also soft closed capsules made of gelatin and a plasticizer, such as glycerol or sorbitol. The hard gelatin capsules may contain the active ingredient in the form of granules, for example in a mixture with fillers, such as lactose, binders, such as starches, and/or lubricants, such as talc or magnesium stearate, and, if desired, stabilizers. In soft capsules, the active ingredient is preferably dissolved or suspended in suitable liquids, such as fatty oils, paraffin oil or liquid polyethylene glycols, it also being possible to add stabilizers.

Suitable rectally utilizable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilizers.

The dose of the active ingredient depends on the mammal species, the age and the individual condition and on the manner of administration. Typically, for an adult mammal of approximately 75 kg, the dosage of the benzodiazepines of the invention or a pharmaceutically acceptable salt is from about 0.75 to about 7500 mg, preferably about 1 to about 1000 mg. Modified dosage ranges for mammals of other sizes and stages of development will be apparent to those of ordinary skill.

All references cited in this patent are hereby incorporated by reference for their relevant teachings. The following Examples illustrate specific embodiments of the inventions, but are not intended to limit the scope of the invention in any way.

EXAMPLES

Example 1

Synthesis of 3',4'-Dideoxy Pyranmycin (RR501)

To avoid the solubility problem, we used azido groups as the surrogate for amino groups. The synthesis of a key intermediate, 3',4'-dideoxyneamine, began from neamine. Neamine was obtained from acid-hydrolysis of neomycin (purchased from Research Organics Inc.), then converted to tetraazidoneamine, 2, using $TfN_3$ and $CuSO_4$ (Scheme 1).[5] The selective protection of the diol was achieved using cyclohexanone dimethylketal. The key transformation is the elimination of diol to alkene. To our surprise, we were unable to locate dideoxygenation methods that are compatible with the presence of azido group and the acid-labile glycoside bond despite numerous documentations. In general, the reported methods for dideoxygenation often require reductive or harsh conditions, for example, the presence of Zn, NaI, and heating from dimesylated compound (Tipson-Cohen method),[10] acid-catalyzed elimination from a diol using ethyl orthoformate (Crank-Eastwood method),[11] $LiAlH_4/TiCl_4$ (McMurry-Fleming method),[12] diphosphorous tetraiodide from diol (Kuhn-Winterstein reaction),[13] $SnCl_2/HCl$,[14] and $PPh_3$ and $I_2$.[15]

Among these reported methods, the method involving mesylated compound and Zn-mediated elimination appeared to be the most applicable one of being modified to meet our needs. Since a triflated hydroxyl group is more reactive than a mesylated hydroxyl group, we expected that the ditriflate can be replaced with a trans diiodide in which, the two iodides are in an anti-parallel configuration. Such a configuration can induce a facile elimination under the catalysis of $I^-$ producing the desired alkene and $I_2$. To avoid complication from the possible addition reaction between the alkene and $I_2$, $Na_2S_2O_3$ was added to reduce $I_2$ into $I^-$ allowing $I_2/I^-$ to function as catalyst. We are pleased to discover that the elimination occurred smoothly as expected providing compounds 4 and 5. Compound 5 was converted to 4 giving an overall yield of ~80%.

Regioselective protection of C-6 hydoxyl group using benzoyl chloride furnished compound 6 in excellent yield (Scheme 2). Compound 6 was glycosylated with the corresponding trichloroacetimidate donor, 7, from the lead structure of our previous work generating the 3',4'-dideoxy pyranmycin adduct RR501.

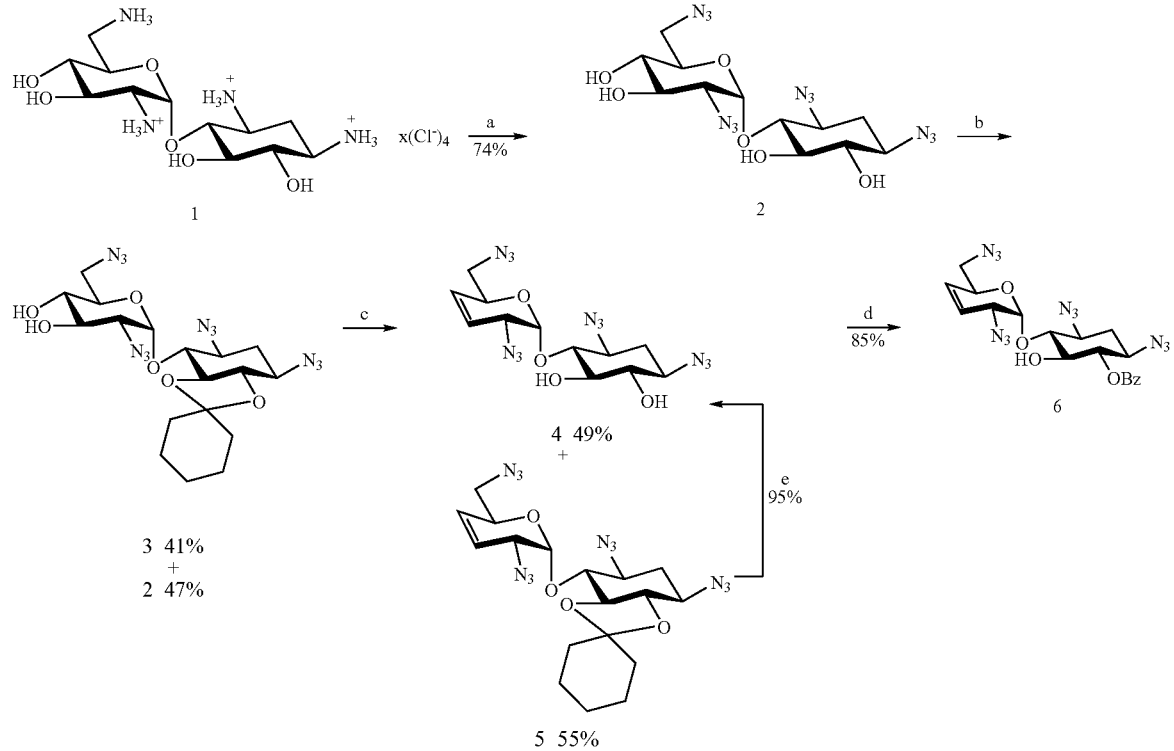

Scheme 1. Synthesis of Neamine Acceptor[a]

[a] Conditions: (a) $TfN_3$, $CuSO_4$, $H_2O$, $CH_2Cl_2$, (b) Cyclohexone dimethyl ketal, TsOH—$H_2O$, $CH_3CN$, (c) (1) $Tf_2O$, pyr., $CH_2Cl_2$; (2) $Na_2S_2O_3$, NaI, acetone, (d) BzCl, $CH_2Cl_2$, -50° C., (e) $H_2O$, HOAc, dioxane, 65° C.

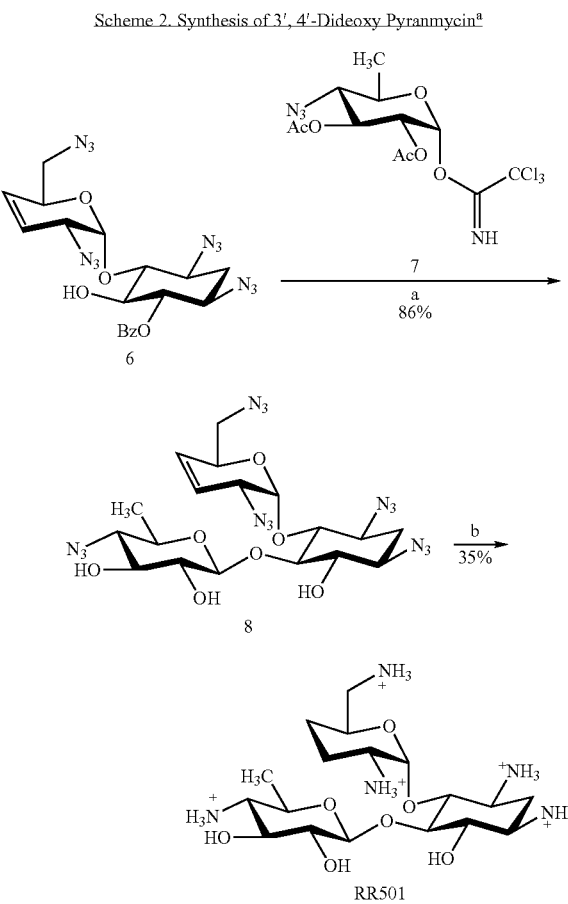

Example 2

Synthesis of Pyranmycin Compounds (with 3',4' hydroxyl) and

Compounds of Example 1 with hydroxyl substitutions at both the $R^1$ and $R^2$ positions are made as described in Reference 4.

Example 3

Synthesis of Pyranmycin, 3',4'-Dideoxy Pyranmycin Compounds with (S)-4-amino-2-hydroxybutyryl in the $R^4$ Position Compounds of Examples 1 and 2 with (S)-4-amino-2-hydroxybutyryl in the $R^4$ position are made as follows (Scheme 3). Compound 10 was obtained from 3 (see Scheme 1) via acetylation of the O-3' and O-4' diols, followed by deprotection of the cyclohexylidene group. Diacylation of O-5 and O-6 diols afforded 11.

A one-pot azido reduction/amine protection was employed to selectively modify the N-1 azido group of 11 (Scheme 4). After hydrolysis of the acyl groups, the desired 1-N-tBoc protected neamine, 15, was synthesized in an overall of 33% along with 3-N-tBoc protected neamine (5%) and 1,3-N-di-tBoc protected neamine (22%) as the minor products. Selective benzoylation of O-6 of 15 yielded 17.

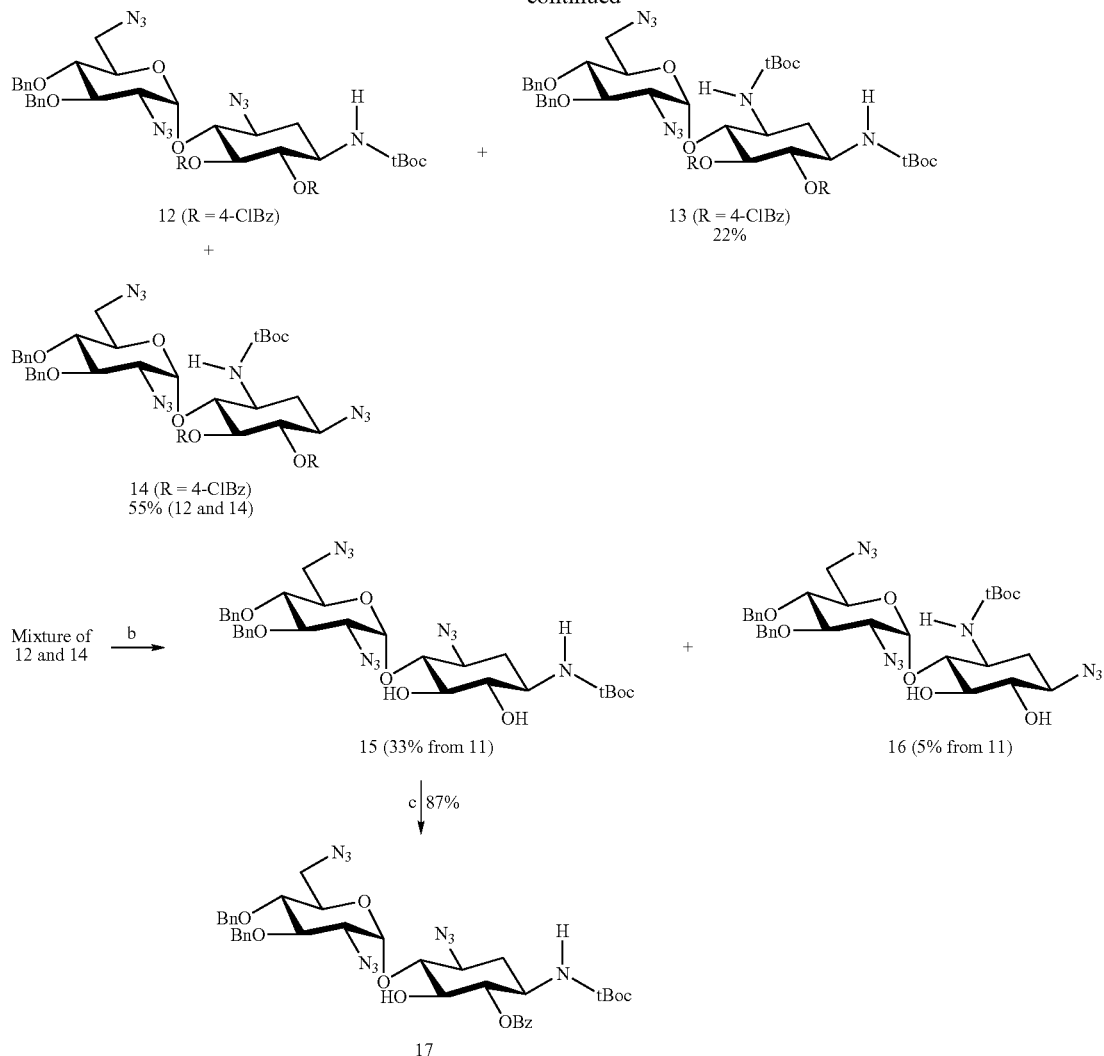

(a) 1.0 M PMe₃ in Toluene (1.2 eq), Boc—ON (3.6 eq), Toluene (dry), -78° C. to R.T.; (b) NaOMe in MeOH (0.5M), MeOH/THF (5/1); (c) BzCl, DIPEA, CH₂Cl₂.

Glycosylation of 17 using 7 as the glycosyl donor followed by NaOMe-mediated hydrolysis afforded 18 (Scheme 5). Deprotection of the tBoc exposed the N-1 amino group, which was coupled with desired side chain, 25, yielded 19. Global deprotection using Staudinger reaction and hydrogenation, followed by ion-exchange offered the final product, JT005, as a chloride salt.

Scheme 5.

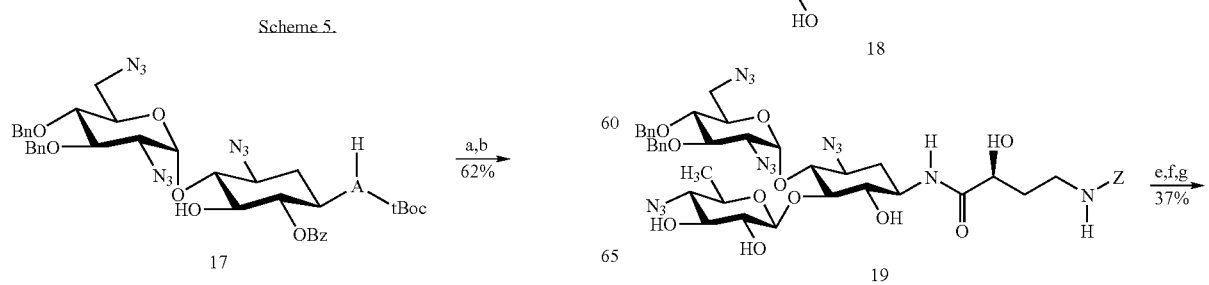

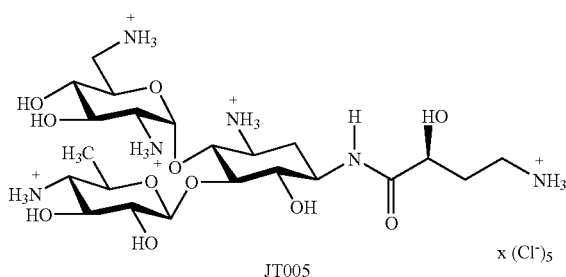

JT005  x (Cl⁻)$_5$ (a) 7, BF$_3$—Et$_2$O, CH$_2$Cl$_2$; (b) NaOMe, THF, MeOH; (c) TFA, CH$_2$Cl$_2$; (d) N-Cbz AHB, EDC, HOBt, DMF; (e) PMe$_3$ THF, H$_2$O; (f) H$_2$, Pd(OH)$_2$/C, HOAc/H$_2$O (1/4); (g) Dowex 1X-8 (Cl⁻ form).

Example 4

Synthesis of 3',4'-Dideoxy Pyranmycin Substituted in the R³ Position

Compounds of Formula 1, including those of Examples 1-3, with additional substitutions at the R3 position are made using commercially available reagents and utilizing known chemical reactions. Any of the following can be substituted at the R3 position:

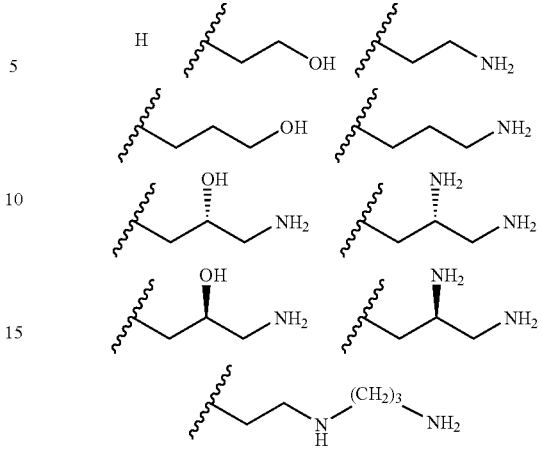

These compounds are made utilizing known alkylation methods. For example, compound 15 can be mono-alkylated using allyl bromide generating 20 (Scheme 6). Ozonlysis of 20 followed by reductive workup afforded 22. Azido substitution of the primary hydroxyl group of 22 provided 23, which can be glycosylated with 7 yealding 24. Global deprotection using hydrolysis, Staudinger reaction, and hydrogenation, followed by ion-exchange offered the final product, JT050, as chloride sale.

II. Synthesis of Pyranmycin with O-6 and N-1 Modifications

Scheme 6. Current synthetic for pyranmycin with O-6 modification

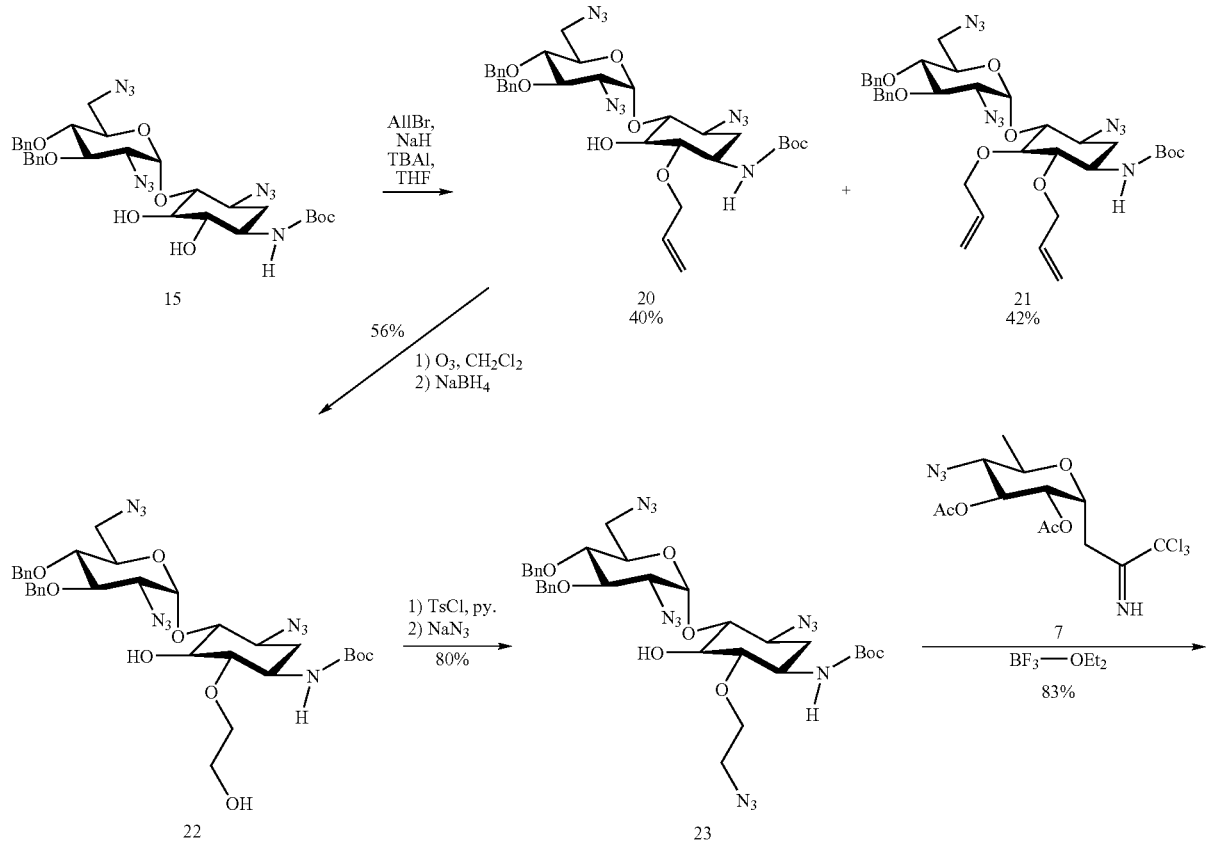

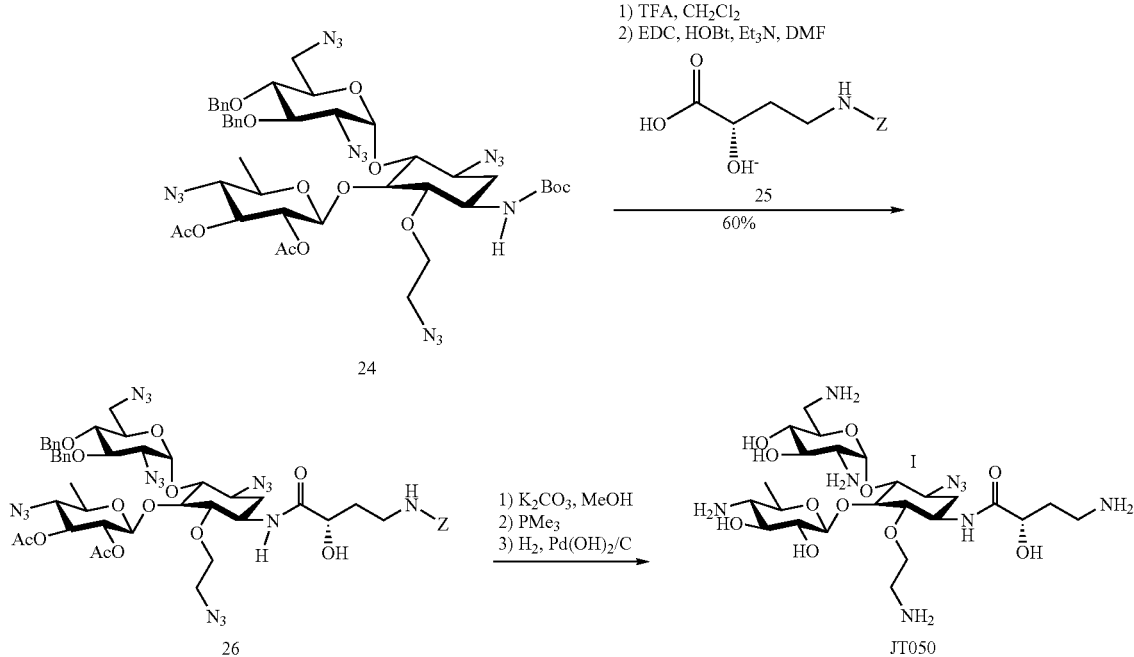

The incorporation of functional groups at O-6 position can begin from compound 20 (Scheme 7). The designed epoxides, 23 and 24 can be obtained from treatment of 20 with mCPBA. Both 23 and 24 can be utilized for the introduction of more functionalities via know procedures, leading to the synthesis of JT054, JT055, JT056, and JT057.

Alternatively, using different but known chemical reagents, compound 20 can be converted into 22 and 29. Compound 22 can be employed for the synthesis of JT051 and JT058 while 29 can be used for the synthesis of JT052 and JT053. Similar strategy can be applied for the synthesis of pyranmycin in other two designs.

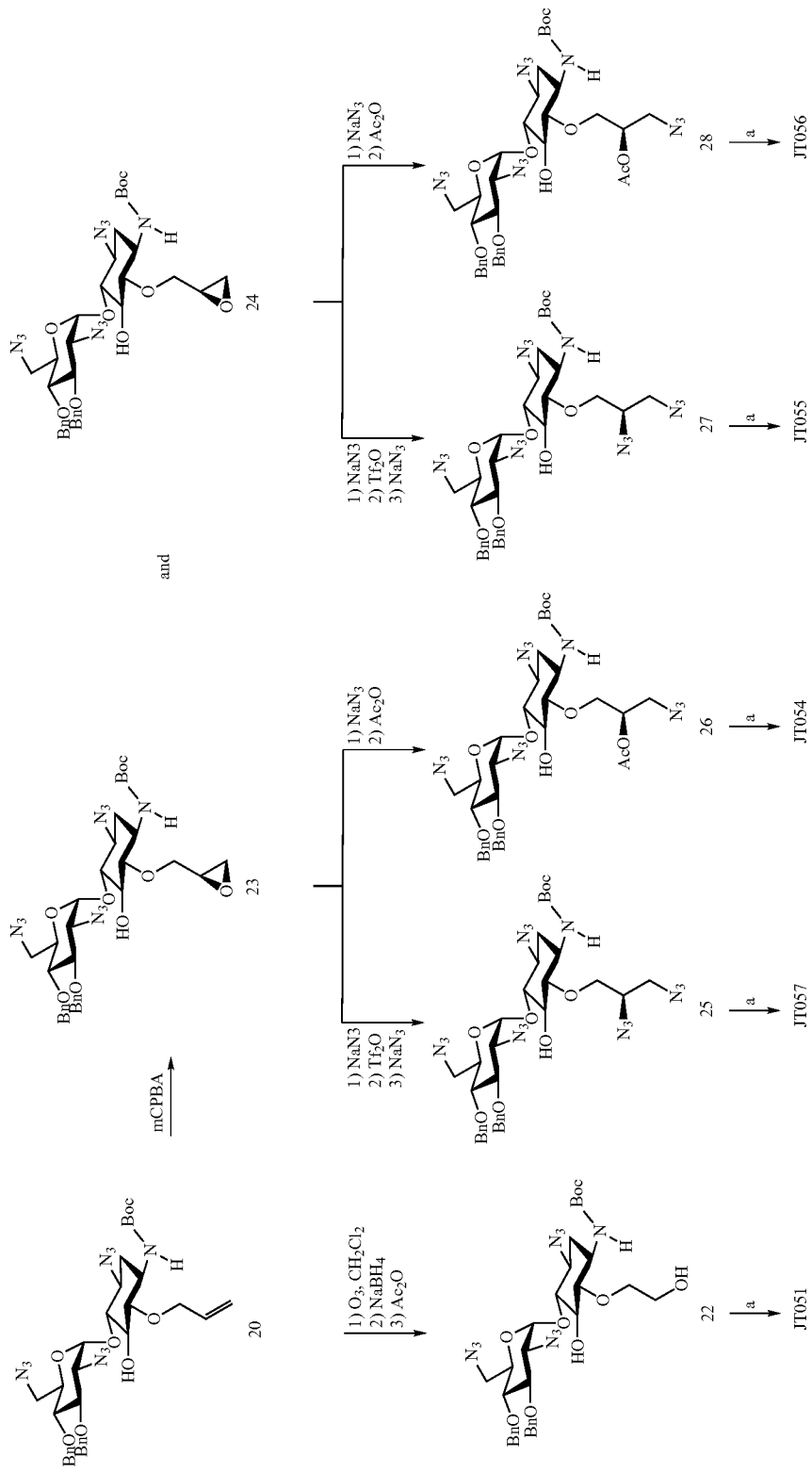

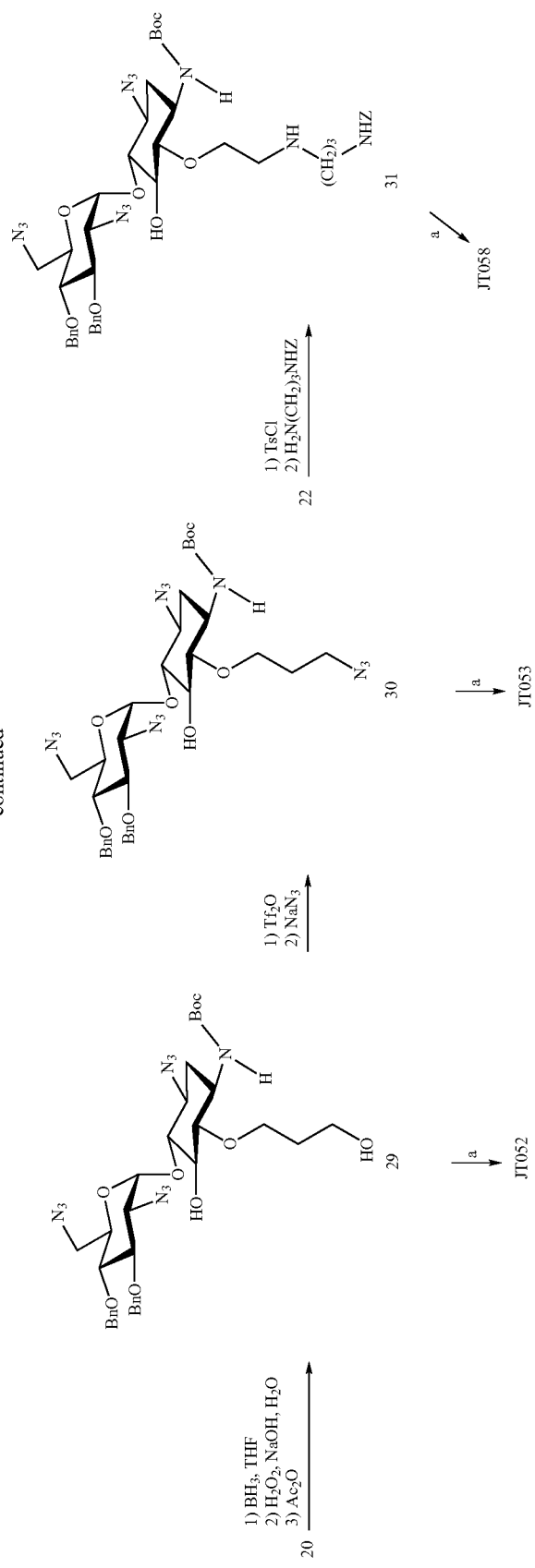

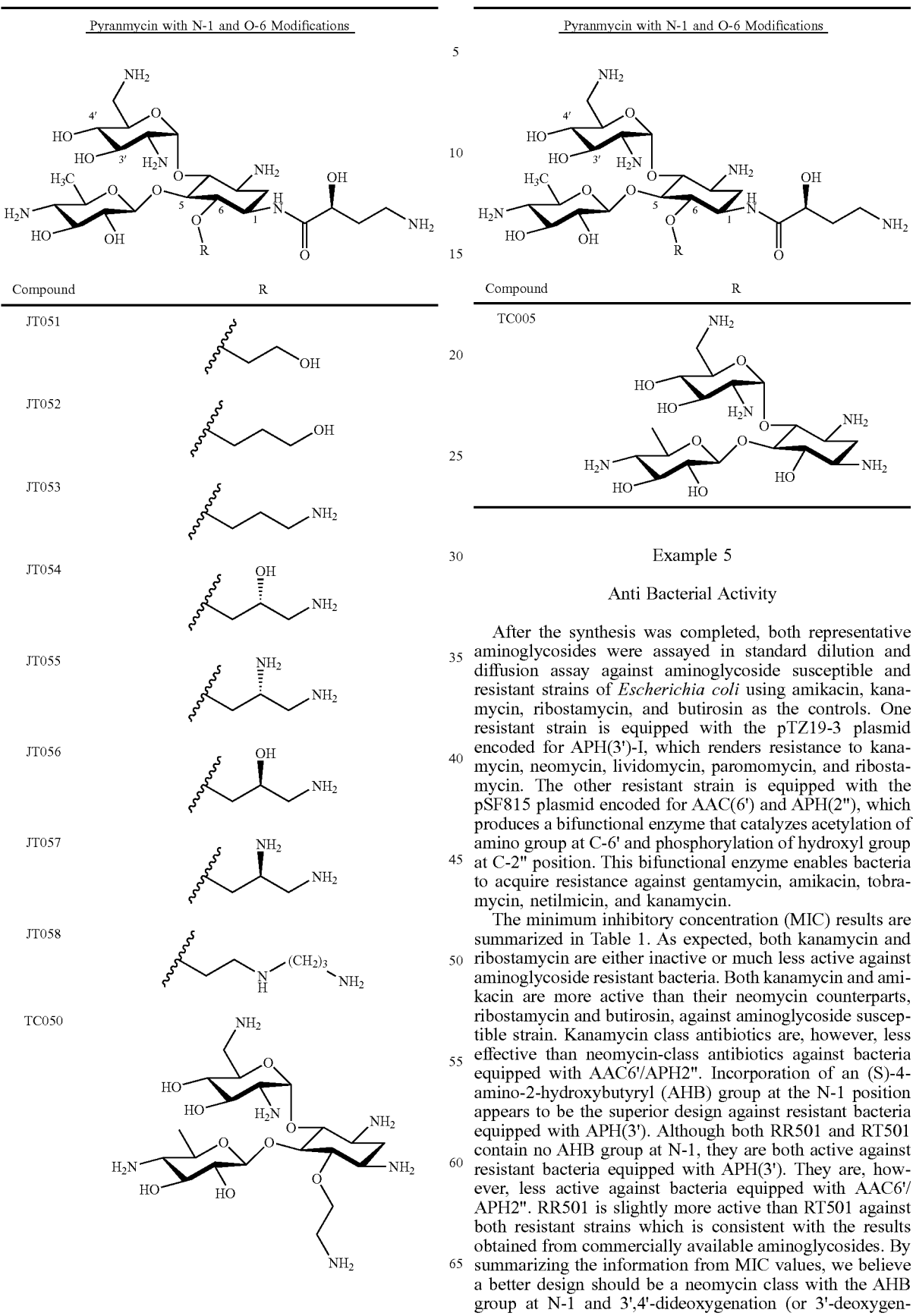

Example 5

Anti Bacterial Activity

After the synthesis was completed, both representative aminoglycosides were assayed in standard dilution and diffusion assay against aminoglycoside susceptible and resistant strains of *Escherichia coli* using amikacin, kanamycin, ribostamycin, and butirosin as the controls. One resistant strain is equipped with the pTZ19-3 plasmid encoded for APH(3')-I, which renders resistance to kanamycin, neomycin, lividomycin, paromomycin, and ribostamycin. The other resistant strain is equipped with the pSF815 plasmid encoded for AAC(6') and APH(2"), which produces a bifunctional enzyme that catalyzes acetylation of amino group at C-6' and phosphorylation of hydroxyl group at C-2" position. This bifunctional enzyme enables bacteria to acquire resistance against gentamycin, amikacin, tobramycin, netilmicin, and kanamycin.

The minimum inhibitory concentration (MIC) results are summarized in Table 1. As expected, both kanamycin and ribostamycin are either inactive or much less active against aminoglycoside resistant bacteria. Both kanamycin and amikacin are more active than their neomycin counterparts, ribostamycin and butirosin, against aminoglycoside susceptible strain. Kanamycin class antibiotics are, however, less effective than neomycin-class antibiotics against bacteria equipped with AAC6'/APH2". Incorporation of an (S)-4-amino-2-hydroxybutyryl (AHB) group at the N-1 position appears to be the superior design against resistant bacteria equipped with APH(3'). Although both RR501 and RT501 contain no AHB group at N-1, they are both active against resistant bacteria equipped with APH(3'). They are, however, less active against bacteria equipped with AAC6'/APH2". RR501 is slightly more active than RT501 against both resistant strains which is consistent with the results obtained from commercially available aminoglycosides. By summarizing the information from MIC values, we believe a better design should be a neomycin class with the AHB group at N-1 and 3',4'-dideoxygenation (or 3'-deoxygenation). Nevertheless, the problem of the acid-labile glycosidic bond between rings II and III will be an obstacle remained to be overcome. Therefore, our design of RR501 that has better stability in acidic media could be valuable for designing new aminoglycosides against a broad spectrum of aminoglycoside resistant bacteria.

TABLE 1

Minimum Inhibitory Concentration of Synthesized Aminoglycosides[a]

| Compounds | E. coli (TG1) | E. coli (TG1) (pSF815)[b] | E. coli (TG1) (pTZ19U-3)[c] |
|---|---|---|---|
| Amikacin | 1 | 1 | 0.5 |
| Kanamycin B | 4 | Inactive | 32 |
| Ribostamycin | 2 | 16 | Inactive |
| Butirosin | 0.5 | 0.5 | 0.5 |
| RR501 | 8 | 4 | 4 |
| RT501 | 8 | Inactive | 4 |
| TC005 | 8 | Inactive | 8 |
| JT005 | 4 | 4 | 4 |
| TC050 | 8 | Inactive | 8 |
| JT050 | 8 | 2 | 4 |

[a]Unit: μg/mL
[b]plasmid encoded for AAC6'/APH2"
[c]plasmid encoded for APH(3')-I Example 6

Synthesis of Pyrankacin

The synthesis of pyrankacin started from the chlorobenzoylation of 2 (16) to yield 3 in Scheme 1 below (entitled "Synthesis of Pyrankacin"), which was then subjected to a selective Staudinger reaction to yield the N-1 Boc-protected compound 4 (Scheme 1 below). Interestingly, the obtained selectivity was even better than when 5,6-di-O-acyl-3',4'-di-O-benzyltetraazidoneamine was employed (17). Hydrolysis of the ester protecting groups followed by selective benzoylation at the O-6 position gave 6. Glycosylation of 6 with 7 (18) followed by the hydrolysis of the acyl groups offered the corresponding trisaccharide, 10. Deprotection of the Boc group and coupling with the (S)-N-carbobenzyloxy-4-amino-2-hydroxybutyric acid yielded 10. Global deprotection and ion-exchange provided the desired final product, which we named, pyrankacin.

Scheme 1. Synthesis of Pyrankacin

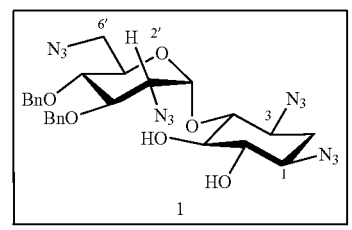

1

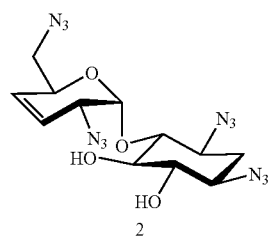

2

4-Chlorobenzoyl chloride, Et₃N, DMAP, CH₂Cl₂
82%

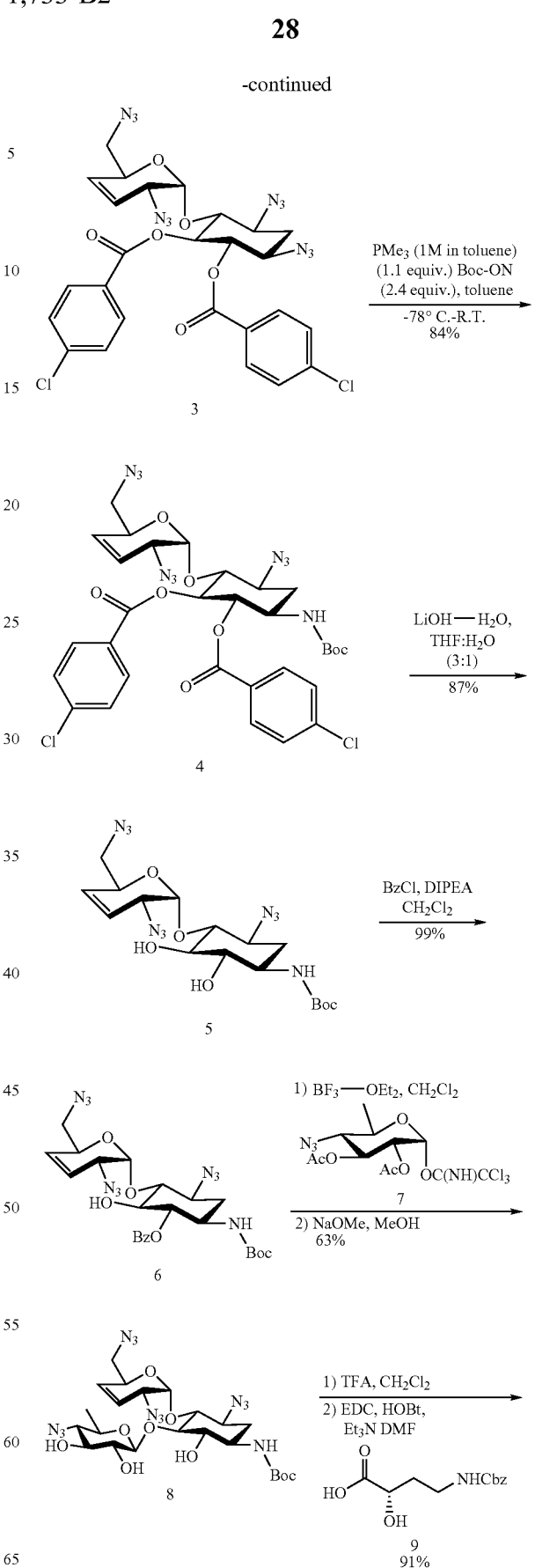

-continued

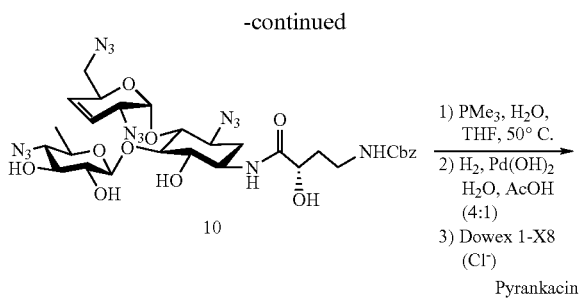

Example 7

Anti Bacterial Activity of Pyrankacin

Pyrankacin was assayed against various strains of bacteria and the minimum inhibitory concentration (MIC) was determined using amikacin, neomycin, butirosin, gentamicin, kanamycin as the controls. (Table 2). Aminoglycoside susceptible *Escherichia coli* (ATCC 25922), *Staphylococcus aureus* (ATCC 25923), and *Klebsiella pneumoniae* (ATCC 13883, resistant to ampicillin, susceptible to aminoglycosides) were used as standard reference strains. *E. coli* (pSF815) and *E. coli* (pTZ19U-3) are laboratory resistant strains using *E. coli* (TG1) as the host. *K. pneumoniae* (ATCC 700603)(19) is a clinical isolate that is resistant to ceftazidime, other β-lactams, and several aminoglycosides (ANT(2″)). *Pseudomonas aeruginosa* (ATCC 27853) that expresses APH(3')-IIb manifests modest resistance toward aminoglycosides (20). Methicillin-resistant *S. aureus* (ATCC 33591) (MRSA) is the leading cause of bacterial infections and a global scourge. Many MRSA strains contain genes encoded for APH(3'), ANT(4'), and AAC(6')/APH (2″), which render the bacteria resistant to many aminoglycosides (21).

From the MIC values, pyrankacin appears to be one with the most prominent broad spectrum antibacterial activity against all the examined strains. For example, for the clinically used gentamicin and amikacin, the former is ineffective against bacteria with the bifunctional enzyme, AAC(6')/APH(2″) and *K. pneumoniae* (ATCC 700603) (entries 3 and 5) while the latter is less active against MRSA (entry 7). Pyrankacin is more active than gentamicin against *E. coli* (pSF815) and *K. pneumoniae* (ATCC 700603) (entries 3 and 5). While being less active than gentamicin against MRSA, pyrankacin is more active than amikacin against the same strain. More interestingly, even pyrankacin can be viewed as a neomycin class aminoglycoside, it is the only active compound against *P. aeruginosa* among JT005 (17), neomycin, butirosin and ribostamycin. The attachment of AHB group at N-1 of kanamycin class aminoglycoside as in the case of amikacin revives the antibacterial activity, while the same modification on butirosin and JT005 does not produce the same effect. This result suggests that a combination of 3',4'-dideoxygenation and N-1 AHB group is essential for neomycin class aminoglycoside to be active against *P. aeruginosa*.

TABLE 2

Minimum Inhibitory Concentrations (MIC) [a]

| entry | strains | amikacin | butirosin | gentamicin | neomycin | ribostamycin | kanamycin B | pyrankacin | RR501 | JT005 |
|---|---|---|---|---|---|---|---|---|---|---|
| 1 | *E. coli* [b] | 1 | 2 | 2 | 4 | 8 | 2 | 4 | ND | ND |
| 2 | *E. coli* (TG1) [c] | 1 | 1 | 2 | 8 | 2 | 4 | 4 | 8 | 4 |
| 3 | *E. coli* (pSF815) [d] | 1 | 0.25 | Inactive [k] | 2 | 16 | Inactive | 1 | 4 | 4 |
| 4 | *E. coli* (pTZ19U-3) [e] | 0.5 | 0.5 | 1 | Inactive | 32 | Inactive | 1 | 4 | 4 |
| 5 | *K. pneumoniae* [f] | 0.5-1 | 0.5 | 8-16 | Inactive | Inactive | Inactive | 1 | 2-4 | 1-2 |
| 6 | *K. pneumoniae* [g] | 1 | 0.5-1 | 1 | 2 | 4 | 1 | 2 | 2-4 | 2 |
| 7 | *S. aureus* [h] | 16 | Inactive | 4 | Inactive | Inactive | Inactive | 8 | 4 | Inactive |
| 8 | *S. aureus* [i] | 1 | 2 | 0.5 | 1 | 8 | 1-2 | 2 | ND | ND |
| 9 | *P. aeruginosa* [j] | 0.5-1 | Inactive | 0.5-1 | Inactive | Inactive | Inactive | 2 | Inactive | Inactive |

[a] Unit: μg/mL,
ND: Not Determined,
[b] *Escherichia coli* (ATCC 25922),
[c] *E. coli* (TG1) (aminoglycoside susceptible strain),
[d] *E. coli* (TG1) (pSF815 plasmid encoded for (AAC(6')/APH(2″)),
[e] *E. coli* (TG1) (pTZ19U-3 plasmid encoded for APH(3')-I),
[f] *Klebsiella pneumoniae* (ATCC 700603),
[g] *K. pneumoniae* (ATCC 13883),
[h] *Staphylococcus aureus* (ATCC 33591) (MRSA),
[i] *S. aureus* (ATCC 25923),
[j] *Pseudomonas aeruginosa* (ATCC 27853),
[k] Inactive is defined as MIC ≧ 32 μg/mL.

REFERENCES

1. For reviewing: (a) Haddad, J; Kotra, L. P.; Mobashery, S. in *Glycochemistry Principles, Synthesis, and Applications*, Wang, P. G. and Bertozzi, C. R. Ed. Marcel Dekker, Inc. 2001; p307-424. (b) Umezawa, H. *Jpn. J. Antibiotics*, 1994, 47, 561-574. (c) Vakulenko, S. B.; Mobashery, S. *Clinical Microbiol. Rev.* 2003, 16, 430-450. (d) Hooper, I. R. *Aminoglycoside Antibiotics* Springer-Verlag 1982, New York.

2. (a) Mingeot-Leclercq, M.-P.; Glupczynski, Y.; Tulkens, P. M. *Antimicrob. Agents Chemother.* 1997, 43, 727-737. (b) Kotra, L. P.; Haddad, J.; Mobashery, S. *Antimicrob. Agents Chemother.* 2000, 44, 3249-3256. (c) Wright, G. D. *Curr. Opin. Microbiol.* 1999, 2, 499-503.

3. Mingeot-Leclercq, M.-P.; Tulkens, P. M. "Aminoglycosides: nephrotoxicity." *Antimicrob. Agents Chemother.* 1999, 43, 1003-1012.

4. (a) Wang, J.; Li, J.; Tuttle, D.; Takemoto, J.; Chang, C.-W. T. *Org. Lett.* 2002, 4, 3997-4000. (b) Chang, C.-W. T.; Hui, Y.; Elchert, B.; Wang, J.; Li, J.; Rai, R. *Org. Lett.* 2002, 4, 4603-4606. (c) Li, J.; Wang, J.; Hui, Y.; Chang, C.-W. T. *Org. Lett.* 2003, 5, 431-434. (d) Elchert, B.; Li, J.; Wang, J.; Hui, Y.; Rai, R.; Ptak, R.; Ward, P.; Takemoto, J. Y.; Bensaci, M.; Chang, C.-W. T. *J. Org. Chem.*, 2004, 69, 1513-1523. (e) Wang, J.; Li, L.; Czyryca, P. G.; Chang, H.; Kao, J.; Chang, C.-W. T. *Bioorg. Med. Chem. Lett.* 2004, 14, 4389-4393.

5. Li, J.; Wang, J.; Czyryca, P. G.; Chang, H.; Orsak, T. W.; Evanson, R.; Chang, C.-W. T. *Org. Lett.* 2004, 6, 1381-1384.

6. (a) Umezawa, H.; Miyasaka, T.; Iwasawa, H.; Ikeda, D.;, Kondo, S. *J. Antibiot.* 1981, 34, 1635-1640. (b) Jikihara, T.; Tsuchiya, T.; Umezawa, S.; Umezawa, H. *Bull. Chem. Soc. Jpn.* 1973, 46, 3507-3510. (c) Tsuchiya, T.; Takahashi, Y.; Endo, M.; Umezawa, S.; Umezawa, H. *J. Carbohydr. Chem.* 1985, 4, 587-611. (d) Umezawa, S.; Umezawa, H.; Okazaki, Y.; Tsuchiya, T. *Bull. Chem. Soc. Jpn.* 1972, 45, 3624-3628. (e) Umezawa, H.; Umezawa, S.; Tsuchiya, T.; Okazaki, H. *J. Antibiot.* 1971, 24, 485-487.

7. (a) Umezawa, S.; Okazaki, Y.; Tsuchiya, T. *Bull. Chem. Soc. Jpn.* 1972, 45, 3619-3624. (b) Canas-Rodriguez, A.; Martinez-Tobed, A. *Carbohydr. Res.* 1979, 68, 43-53. (c) Matsuno, T. Yoneta, T.; Fukathu, S. *Carbohydr. Res.* 1982, 109, 271-275. (d) Woo, P. W. K.; Haskell, T. H. *J. Antibiot.* 1982, 35, 692-702.

8. (a) Koch, K. F.; Rhoades, J. A. *Antimicrob. Agents Chemother.* 1971, 309-313. (b) Koch, K. F.; Davis, F. A.; Rhoades, J. A. *J. Antibiot.* 1973, 26, 745-751.

9. Kondo, S.; Iinuma, K.; Yamamoto, H.; Maeda, K.; Umezawa, H. *J. Antibiot.* 1973, 26, 412-415.

10. (a) Tipson, R. S.; Cohen, A. *Carbohydr. Res.* 1965, 1, 338. (b) Suami, T.; Nishiyama, S.; Ishikawa, Y.; Katsura, S. *Carbohydr. Res.* 1977, 53, 239-246.

11. Crank, G.; Eastwood, F. W. *Aust. J. Chem.* 1964, 17, 1392.

12. McMurry, J. E.; Fleming, M. P. *J. Org. Chem.* 1976, 41, 896-897.

13. Kuhn, R.; Winterstein, A. *Helv. Chim. Acta,* 1928, 11, 113.

14. Kuhn, R.; Krauch, H. *Chem. Ber.* 1955, 88, 309-315.

15. Alcòn, M.; Poch, M.; Moyano, A.; Pericàs, M. A.; Riera, A. *Tetrahedron: Asymmety* 1997, 8, 2967.

16. Rai et al, (2005) J. Carbohydr. Chem, 24:131-143

17. Li, et al., (2005) Org. Lett. 7:3061-3064

18. Chang et al., (2002) Org. Lett. 4:4603-4606; and Elchert et al., (2004) J. Org. Chem. 69:1513-1523

19. Rasheed et al, (200) Antimicrob. Agents Chemother. 44:2382-2388.

20. Hachiler et al, (1996) Antimicrob. Agents Chemother. 40:1254-1256

21. Ida et al, (2001) J. Clin. Microbiol. 39:3155-3121

What is claimed is:

1. An antibacterial compound comprising a compound having Formula 1

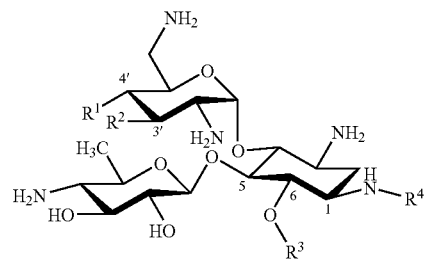

Formula 1 wherein

R1 and R2 are both H

R3 is selected from the group consisting of

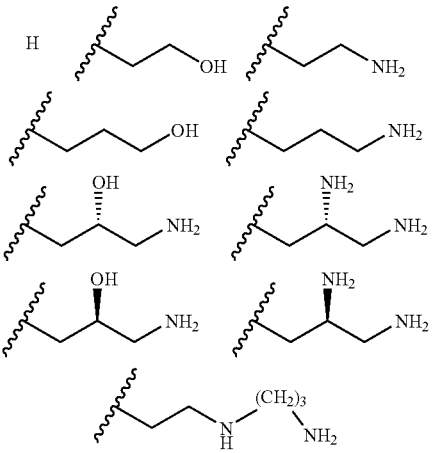

And R4 is either H or

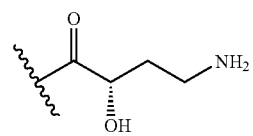

AHB: (S)-4-amino-2-hydroxybutyryl.

2. A compound selected from the group consisting of

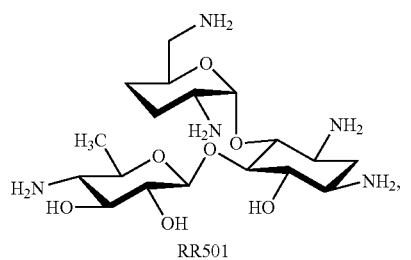

RR501

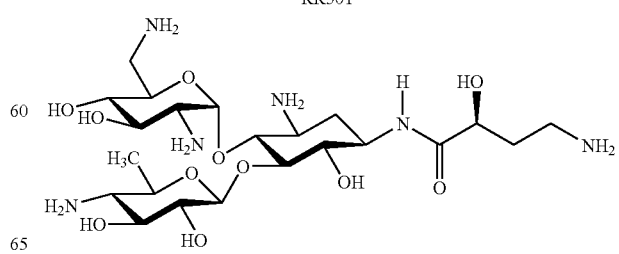

JT005

-continued

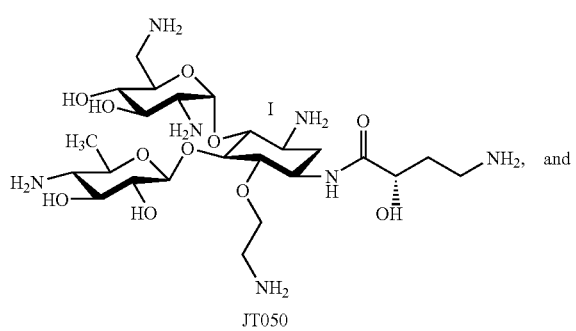
JT050

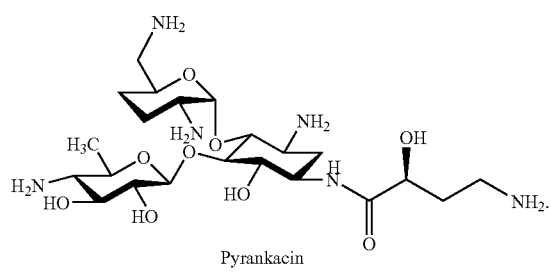
Pyrankacin

3. A method of treating a bacterial infection in a mammal comprising administering to said mammal an antibacterial effective amount of a compound according to claim 1.

4. A method of treating a bacterial infection in a mammal comprising administering to said mammal an antibacterial effective amount of a compound according to claim 2.

5. An antibacterial compound comprising a compound having Formula 1

Formula 1

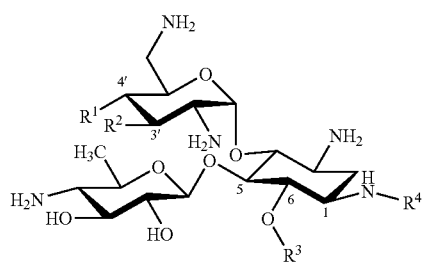

wherein
R1 and R2 are both OH
R3 is selected from the group consisting of

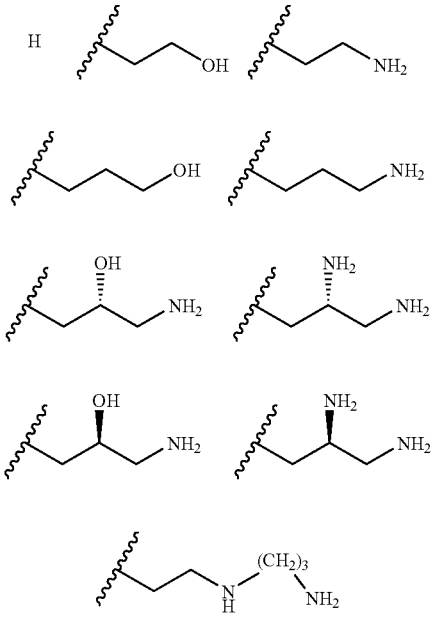

and R4 is

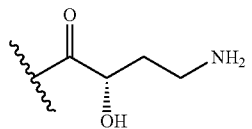

AHB: (S)-4-amino-2-hydroxybutyryl.

6. A method of treating a bacterial infection in a mammal comprising administering to said mammal an antibacterial effective amount of a compound according to claim 5.

* * * * *